United States Patent [19]
Liss et al.

[11] Patent Number: 5,851,223
[45] Date of Patent: Dec. 22, 1998

[54] COMBINATION NON-INTRUSIVE ANALGESIC NEUROAUGMENTIVE SYSTEM AND METHOD TRIPLE-MODULATED GIGATENS WITH OPTIONAL BIPOLAR SPIKE

[75] Inventors: Saul Liss, Hawthorne; Bernard Liss, Glen Rock, both of N.J.; C. Norman Shealy, Fair Grove, Mo.; Grigoriy S. Litvinov; Valeri Lobarey, both of Kiev, Ukraine

[73] Assignee: Medi Consultants, Inc., Paterson, N.J.

[21] Appl. No.: 389,499

[22] Filed: Feb. 16, 1995

Related U.S. Application Data

[63] Continuation-in-part of Ser. No. 227,014, Apr. 13, 1994, Pat. No. 5,571,149, which is a continuation-in-part of Ser. No. 82,131, Jun. 23, 1993, abandoned, which is a continuation-in-part of Ser. No. 877,873, May 4, 1992, abandoned, which is a continuation of Ser. No. 703,610, May 21, 1991, Pat. No. 5,109,847.

[51] Int. Cl.[6] .................................................. A61N 1/18
[52] U.S. Cl. .............................................. 607/46; 607/72
[58] Field of Search ................................... 607/66, 72, 73, 607/74, 46

[56] References Cited

U.S. PATENT DOCUMENTS

5,421,817  6/1995  Liss et al. ................................. 604/20

Primary Examiner—Scott M. Getzow
Attorney, Agent, or Firm—Hopgood, Calimadfe, Kalil & Judlowe

[57] ABSTRACT

This invention provides a system and apparatus for treating neurally responsive conditions by use of a novel combined waveform in combination with, and preferably modulated onto, a gigaTENS waveform administered to a patient. This modulated combined waveform can also be administered synchronously or asynchronously with a conventional mono- or bipolar spiked waveform, useful for TENS applications and/or for stimulatory input to the patient.

17 Claims, 8 Drawing Sheets

FIG. 1A

CARRIER FREQUENCY
15 KHz MONOPOLAR

FIG. 1B

1st MODULATOR
15 Hz

FIG. 1C

2nd MODULATOR
500 Hz

FIG. 1D

TYPICAL COMBINED
WAVEFORM (BIPOLAR)

FIG. 1E

BIPOLAR SPIKE/TENS

FIG. 1F

TENS FREQ.

FIG. 1G

GHz FREQ.

FIG. 2A

CARRIER FREQUENCY
3.3 KHz MONOPOLAR

FIG. 2B

1st MODULATOR
10 Hz

FIG. 2C

2nd MODULATOR
100 Hz

FIG. 2D

TYPICAL COMBINED
WAVEFORM (BIPOLAR)

FIG. 2E

BIPOLAR SPIKE/TENS

FIG. 2F

TENS FREQ.

FIG. 2G

GHz FREQ.

COMBINATION NON-INTRUSIVE ANALGESIC NEUROAUGMENTIVE SYSTEM AND METHOD TRIPLE-MODULATED GIGATENS WITH OPTIONAL BIPOLAR SPIKE

This application is a continuation-in-part of application Ser. No. 227,014, filed Apr. 13, 1994, now U.S. Pat. No. 5,571,149, which is a continuation-in-part of applications Ser. No. 082,131, filed Jun. 23rd, 1993 now abandoned, a continuation-in-part of application Ser. No. 877,873, filed May 4, 1992, now abandoned, which is a continuation of application Ser. No. 703,610, filed May 21, 1991, now U.S. Pat. No. 5,109,847, the disclosures of which are all incorporated herein by reference.

BACKGROUND OF THE INVENTION

1. The Field of the Invention and Related Applications

The invention of our prior application, now U.S. Pat. No. 5,109,847, generally relates to an apparatus that modulates the neurological responses associated with certain biological dysfunctions, neural pain, and pain caused by blood flow deficiency. More specifically, it is an apparatus and system for the treatment of selected pain and/or neural dysfunction-induced maladies.

The invention of our prior application Ser. No. 127,163, now U.S. Pat. No. 5,421,817, relates to an apparatus for the topical iontophoretic administration of medication for the treatment of various conditions, and an apparatus for modulating neural responses using an additional modulation frequency.

The present application relates to further improvements thereof; more specifically, to body and/or cranial stimulation using a triple-modulated TENS (transcutaneous electrical nerve stimulation), the TENS operating in the gigahertz frequency range (millimeter wavelength) and the modulating frequencies including those of the prior application, and preferably also including a sensory stimulation in combination therewith.

2. The State of the Art

The sensation of pain is associated with numerous physiological and psychological ailments and is a universal experience of all complex living organisms. Pain, as the mental manifestation of a neurological response, is an important biological attribute and is critical to living and enabling a person (or other likewise sentient animal) to understand dangers in the environment and to adapt thereto. Concomitant with this important role, the alleviation of pain has been a fundamental goal of medicine and philosophy for as long as the medical profession has existed. Indeed, the ability to control the neurological pathways through which pain is conveyed has made complex procedures far simpler to implement and much less traumatic to the patient.

There is a class of neurological response which is associated with pain that does not correspond to or act as a warning for a particular physical damage or biological dysfunction. In fact, many biologically important transitions are characterized by significant pain, such as the withdrawal period of an addict, during which time the addict's system is depleted of a specific endogenous narcotic. Other mental conditions which are neurologically response-dependent conditions include depression, hypertension, causalgia pain, insomnia and jet lag. Analogous to pain being an indication that the local environment is being dangerous, occurrences such as jet lag and drug withdrawal are both essentially a severe change in a person's environment.

The importance of the ability to control neurological response and associated perceptions of pain and distress has led to the development of many pain control methodologies. The most common of which employs bio-active chemical agents that act to block neural transmission pathways within the body. These are designed to operate locally for spot treatment or broadly for generalized control or inhibition of pain response throughout the body. Chemical interference with pain signals has broad based appeal, but in many instances is unacceptable. For example, some chemicals have toxic side affects or cause allergic reactions to certain patients, and toxic side effects are not uncommon when two or more drugs are used in combination (whether or not for treating the same condition). For more chronic ailments, such as chronic migraine headache syndrome, repeated absorption of chemical narcotics may reduce the associated pain, but at unacceptably high costs associated with interference with routine activities, addiction, and/or toxicity of the narcotic.

In view of the problems associated with chemical pain control, efforts have abounded to discover treatment approaches which would not involve pharmacological (chemical) interference with neural transmitters in the body. One approach that has recently sparked tremendous interest is the use of low power electrical stimulator devices capable of passing currents across key neural transmitter junctions in the body and thus effecting a blockage of neurological pathways which are inducing messages of pain to the brain. A practical implementation of this approach is disclosed in U.S. Pat. No. 3,902,502 to Liss et al.; the teachings of which are herein incorporated by reference.

The system disclosed in the '502 patent presented a pulsed direct current waveform having a high frequency carrier modulated by a single low frequency modulation. It was discovered that this waveform was particularly successful at controlling symptoms of certain neurological disorders.

Although effective for its applied treatment, many electrical stimulatory devices are limited to certain applications and lack the requisite flexibility for broad-based appeal. In addition, a drawback to the use of electrical stimulation to control pain is the concern by patients and others about the impact of power dissipation on the patient. Although low current, the power dissipation of many of the electrical stimulation devices is still quite significant. Efforts to reduce the applied power have resulted in stimulation devices with little or no physiological impact.

There has been, therefore, a search for new electrical stimulation devices characterized by exceptional pain management capabilities while reducing the overall patient exposure to electrical energy.

It is also clear that pain can be caused by organic physiologic conditions, trauma, infections, and the like. While systemic analgesic agents have been used with some success, it is often desirable to attempt administration directly to the area of the patient where the medication is required. This concept also has application to the administration of a wide variety of pharmacological agents. For example, Joseph Kleinkort delivered a presentation almost a decade ago at the USAFE Medical Convention in Garmisch, Germany, in which he described iontophoretic administration of hydrocortisone; the technique was referred to as transionic injection. Using two moistened electrodes and a particular type of micronized hydrocortisone dispersed in a petrolatum ointment base, it was found that transionic injection was as effective as percutaneous injection. The apparatus used by Kleinkort provided an electrical waveform to the electrodes which consisted of a carrier frequency of 12–20 KHz and a modulation frequency of 8–20 Hz. More recently, Sibalis in U.S. Pat. No. 5,135,478, the disclosure of which is incorporated herein by reference, described an electrical transdermal drug applicator which provides a particular waveform to counteract the apparent decrease in the amount of the pharmaceutical delivered as the duty cycle of the apparatus increases (i.e., the time during which current is "on" relative to the time current is "off"). Sibalis provides a waveform to the electrodes which comprises a negative conditioning pulse and a sequence of different waveforms which dilate blood vessels, impede coagulation and vasoconstriction, and thereby allow for better transdermal delivery of the drug. The complex waveform generally uses an AC carrier frequency of 1.5–3.5 MHz, a pulse width of 1.25–11.25 ms, and is modulated by both an AC modulated square wave at 250 Hz and a second AC modulator at 570–870 Hz.

In what might appear to be in contrast to such rigor, there has been an increased awareness (in the Western world) of various non-western medical techniques, include acupuncture, Chakra, Shiatsu, and the use of "trigger points" in the body through which mediation of body "imbalances" or ailments is effected. Nevertheless, stimulation of the body through such techniques typically takes the form of mechanical energy (e.g., massage, manipulation, or pins inserted into the skin) or thermal energy (e.g., pins with a heat source (often comprised of incense or a botanical composition that will smoke) or hot, wet heat).

There is presently still a need for improved apparatus and techniques for alleviating pain and discomfort. Further, there is a need for an integration of various techniques for treating pain and other discomfort, and especially where the techniques are from medical philosophies that are diverse if not also contradictory (e.g., western and eastern medicine).

SUMMARY AND OBJECTS OF THE PRESENT INVENTION

This invention may be summarized, at least in part with reference to its objects.

It is, therefore, an object of the present invention to provide an apparatus for the selective generation of low current nerve stimulation waveforms configured to control pain and/or reduce the symptoms of certain neurological dysfunctions.

It is another object of the present invention to provide an apparatus for generating a complex waveform that when applied to a patient involves very low power dissipation.

It is a further object of the present invention to provide a pain control system that includes a means for creating a complex waveform and a data processing means for managing and recording the implementation of that waveform.

It is yet another object of the present invention to provide a method for low power, electrically induced analgesic treatment by the placement of at least two electrodes on selected neurologically important sites and the controlled introduction of a complex waveform for a predetermined time forming a treatment regimen.

It is still another object of the present invention to provide a method for treating the neurological dysfunctions associated with such ailments as diabetic neuropathy, depression, migraine headaches, PMS, and drug withdrawal.

The above and other objects of the present invention are realized in a specific illustrative electrical stimulator device.

This device includes a small DC power source and a means for converting the current output of the power source into a complex waveform as an output across two or more electrodes attached to the patient's body. The complex waveform includes a carrier frequency with at least two low frequency modulations, the result of which is used to modulate a TENS application in the gigahertz regime. This complex waveform may be further modulated in a synchronous or asynchronous mode using a conventional monopolar or preferably bipolar spike waveform. Typical frequencies for the bipolar spike waveform are $2^n$ where $0<n<8$, or a randomly varying selection thereof, or a frequency between 1 and 256 Hz, or a continuously varying frequency in the range between 1 and 128 Hz or 60 to 120 Hz. The carrier frequency will preferably range between 1 KHz and 300 GHz. The first modulation to this carrier wave will have a frequency between 0.01 and 199 kilohertz (i.e., between 10 Hz and 199 KHz). The second modulation to the carrier will have a frequency range between 0.1 and 300 kilohertz (i.e., between 100 Hz and 300 KHz). An optional third modulation to the carrier will have a frequency in the range between about 0.1 and 1,000 Hz. Each modulation to the carrier is preferably a pulse train in the form of a square waveform. This resulting complex waveform of three components is then used to modulate (i.e., triple modulate) a millimeter wave signal in the GHz range.

The placement of the electrodes will depend on the ailment of the subject of treatment and the chosen philosophy or discipline of the care provider (e.g., Eastern, Western, Chakra, acupuncture, homeopathic, etc.). The frequency of treatment will depend on the severity of the pain or dysfunction.

In accordance with the varying aspects of the present invention, the stimulator device may include a digital data processor and stored programming for enhanced implementation of the prescribed treatment or lumped constant components. In this manner, the program controlling the output of the stimulator will prevent use beyond a number of times and beyond the time set for each use. The limits of number of uses and of length of time for each use will be set by the prescribing physician. This promotes and enhances the use of expressly developed treatment regimens by a prescribing physician. The patient's progress can be compared to patient compliance in the context of continuing the prescription or altering same on behalf of the patient.

One object of our invention is to minimize the amount of electrical energy which must be applied to the patient to enable a suitable dosage of the drug to be administered.

Yet another object of the invention is to avoid harsh sensation response to the electrical energy, thereby improving patient comfort and compliance with the procedure. On the other hand, many patients find it desirable to experience some level of sensory input (e.g., to know the apparatus is working), and so this invention in another embodiment provides the patient with a mild sensory stimulus indicative of the functioning of the apparatus.

The foregoing features of the present invention may be more fully understood in view of the illustrative description presented below and the claims.

DESCRIPTION OF PREFERRED EMBODIMENTS

Discussing the present invention first in overview, it is a fundamental desideratum to provide a portable non-invasive analgesia inducing apparatus that exhibits a selectively developed complex waveform of electrical output. This output is applied between at least two contact probes for generating intracorporal current. The placement of the probes will depend on the treatment regimen. For example, migraine headache syndrome may involve the placement of the contacting probes on each side of the patient's cranium, one at the primary site of pain and the second at the contralateral trapezius insertion. Other locations may include intraoral, e.g., for local analgesia to control the pain associated with a dental restoration procedure.

Although the theory describing the underlying pain control phenomenon is not well known or, for that matter, even established, and while not desirous of being constrained to a particular theory, it is generally believed that the introduction of an intracorporal current acts upon the electrically conducted neural transmitters of the patient. It has been discovered that the particular complex waveform of the present invention when applied to a patient creates distinct changes in the blood plasma and cerebral spinal fluid concentration of such compounds as melatonin, serotonin, beta endorphin, norepinephrine and cholinesterase which are highly correlated with the pain/pleasure centers of the central nervous system.

In operation, the present invention involves two functional attributes. The first involves the generation of the complex waveform of a select signature. The second attribute is directed to the implementation of the treatment in a delineated treatment regimen.

Figure 1A:
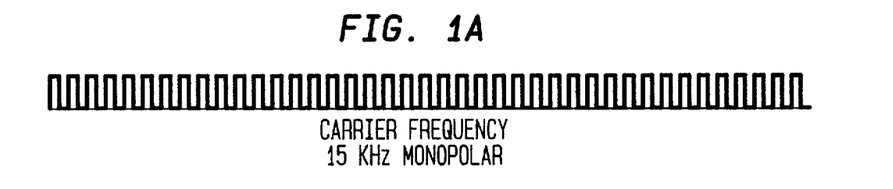
FIGS. 1A–1G are representations of sample carrier, modulation, stimulatory TENS, and composite waveforms utilized in one embodiment of the present invention.
Figure 1B:
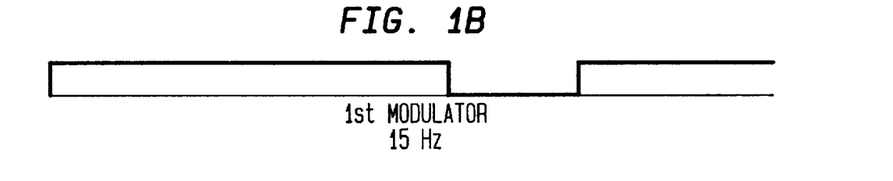
Figure 1C:
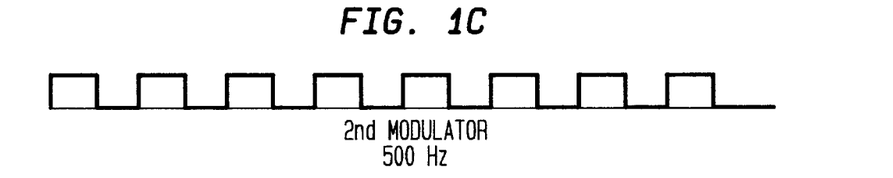

With the above overview in mind, attention is first directed to FIGS. 1A–1F which presents the various components of the complex waveform of the present invention. More particularly, and starting with FIG. 1A, a graphical representation is provided of the carrier frequency for one specific time segment. In this representation, the carrier frequency equals 15 kilohertz. The amplitude is 40.0 volts peak max (DC) with a duty cycle of 50%. The waveform contains 25 bursts of 15 pulses for each burst. The period for each burst is 2 milliseconds and the period for each pulse is 66.7 microseconds. For each, the burst and the pulse, the duty cycle is 50% on time. Continuing, FIG. 1B presents the first modulation to the carrier frequency. In this example, the first modulation has a frequency of 15 Hertz and a duty cycle of 75%. The second modulation is depicted in FIG. 1C. The second modulation has a frequency of 500 Hertz and a 50% duty cycle. Continuing through FIG. 1D, the complex waveform combining the components depicted in FIGS. 1A through 1C are presented.

The complex waveforms of the present invention may be generated with sinusoidal, sawtooth, hyperbolic or other wave shapes; for simplicity and clarity, the waveforms presented in FIGS. 1A through 1D and further discussed below have been exemplified by simple square waves.

A cycle for the waveform will consist of 50 milliseconds "on" time, in which the pulses for that frequency combination are generated, and an "off" time of 16.7 milliseconds.

Figure 1D:
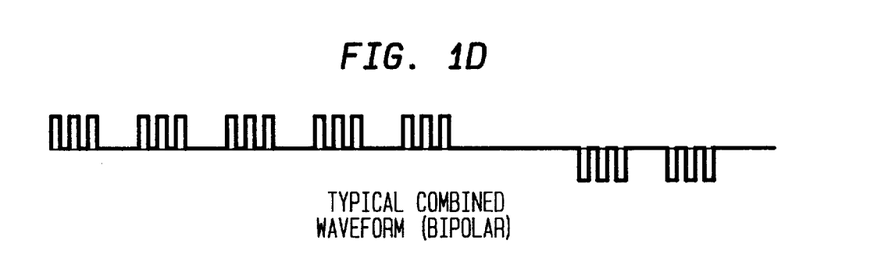

Finally, in FIG. 1D, a complex waveform according to the present invention is provided, in which the polarity of the output is switched from positive to negative on a periodic basis, e.g., 67 ms, resulting in a bipolar waveform.

For purposes of rough approximation, the energy dissipation in using the present invention is represented by the area under the pulses depicted in FIG. 1D. It can, therefore, be recognized that by adding the second modulation, having a 50% duty cycle, results in a 50% decrease in power dissipation.

In another particular embodiment, wherein a monopolar waveform is used, the monopolar stimulation contains a 15 KHz square wave carrier which is rectified and which varies in current (via intensity adjustment) from zero to a maximum of about 4 ma. The first modulating signal of 15 Hz provides an "on" time of 50 ms and an "off" time of 16.7 ms. The second modulating signal of 500 Hz changes the "on" time series of the 15 KHz carrier pulses (750 pulses in 50 ms) into 25 minibursts of 15 pulses each of the 15 KHz carrier signal (375 pulses in the same 50 ms).

In yet another embodiment wherein a bipolar stimulation is used, the bipolar waveform can be composed of the same just-aforementioned frequency specification, with each basic 15 Hz signal alternated positively and then negatively. In this manner, the first 66.7 ms period (50 ms of "on" time and 16.7 ms of "off" time) is a given voltage and the next 66.7 ms period is a voltage of the same absolute value but of the opposite sign.

In summary, the carrier frequency will preferably range between 1 KHz and 300 GHz. The first modulation to this carrier wave will have a frequency between 0.01 and 199 kilohertz (i.e., between 10 Hz and 199 KHz). The second modulation to the carrier will have a frequency range between 0.1 and 300 kilohertz (i.e., between 100 Hz and 300 KHz). Preferred combinations for these three frequencies, and as also shown in the figures, include: 15 Hz, 500 Hz, and 15 KHz (FIGS. 1A–G); and 10 Hz, 100 Hz, and 3.3 KHz (FIGS. 2A–G); all values are preferably ±2%.

As noted in the above U.S. Pat. No. 5,109,847, an optional third modulation of the carrier wave having a frequency range of 0.1 Hz to 1,000 Hz, more preferably 1–50 Hz, and most preferably 5–25 Hz can be utilized.

Figure 1E:
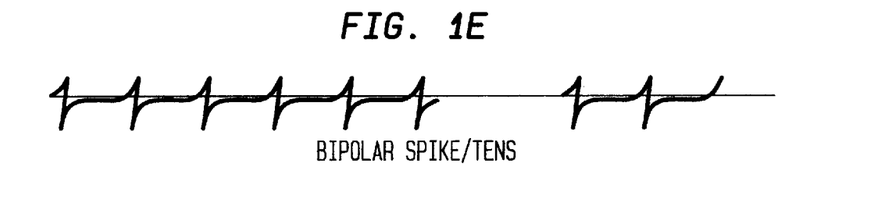
Figure 1F:
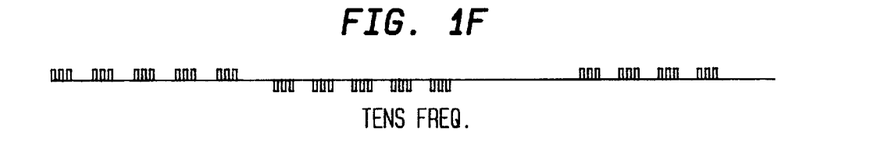

In accordance with the present invention, the combined waveform, such as shown in FIG. 1D, is used to modulate a TENS signal, shown in FIG. 1E, or a stimulatory signal, administered to the patient. TENS devices are commonly known and used (e.g., as described by Katims, in U.S. Pat. No. 4,305,402, Rossen, in U.S. Pat. No. 4,989,605, the disclosures of which are incorporated herein by reference, and others), and by this invention the application of a TENS signal having conventional frequencies and durations is administered to a patient and modulated by means of the aforedescribed combined waveform. Two types of TENS devices are recognized by the American National Standard for Transcutaneous Electrical Nerve Stimulators #NS4 (a standard developed by the Assn. for the Advancement of Medical Instrumentation and approved by ANSI). One standard type of TENS device creates an accommodative or habituating condition that can be controlled by the patient; this type is believed to provide a counter-stimulation signal that is able to overload the body's one pain-communicating signal. Another type of conventional TENS device involves microcurrent stimulation ("MENS"). Particularly preferred TENS frequencies are $2_n$ where 0<n<8 (i.e., 1, 2, 4, 8, 16, 32, 64, and 128 Hz) and the frequency remains constant, or the frequency changes randomnly among those between one and 256 Hz in either a continuous or discontinuous manner (preferably continuous), or is some constant frequent between one and 256 Hz or one randomnly and continuously or discontinuously varying therebetween (or between 60 and 120 Hz). Further, this TENS signal may be administered totally asynchronously with any of the other signals (i.e., totally unmodulated), or may be synchronous with one or more of the other simple or complex waveforms and thus be modulated along therewith.

Figure 1G:
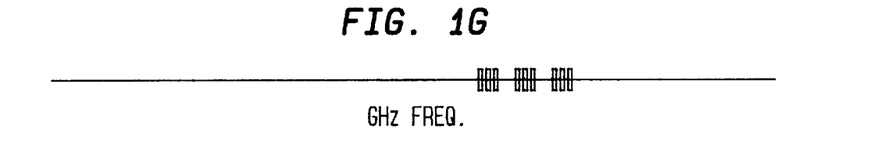
Figure 2A:
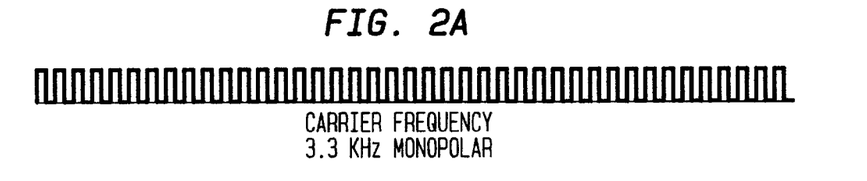
FIGS. 2A–2G are representations of sample carrier, modulation, stimulator TENS, and composite waveforms utilized in another embodiment of the present invention.
Figure 2B:
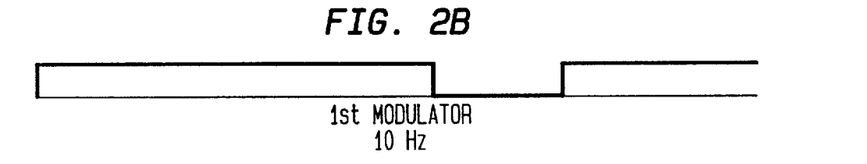
Figure 2C:
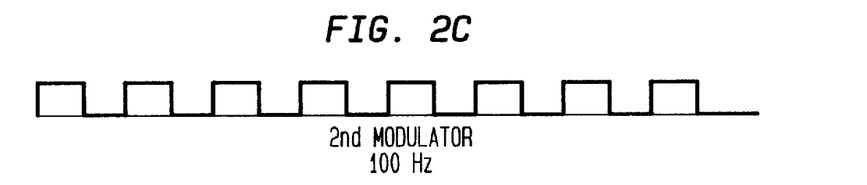
Figure 2D:
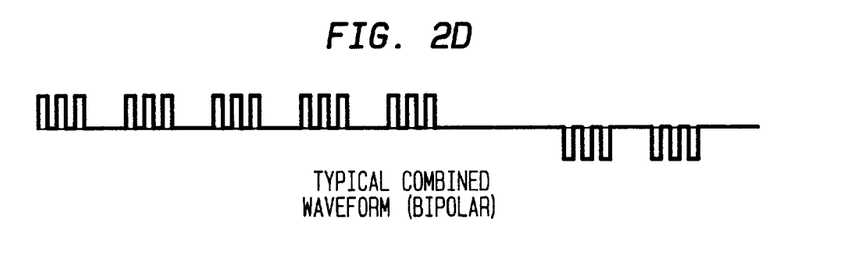
Figure 2E:
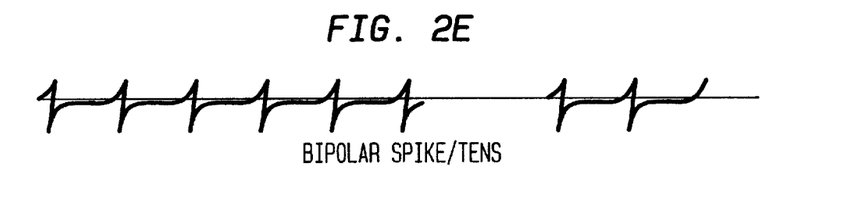
Figure 2F:
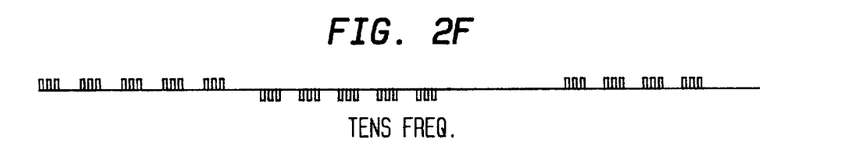
Figure 2G:
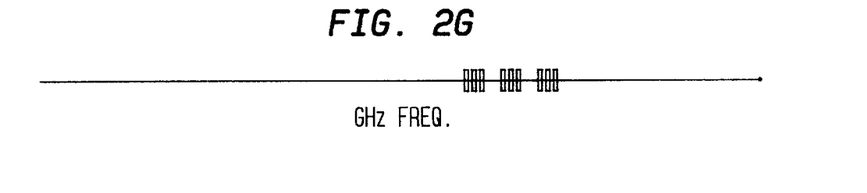

In yet another embodiment of the present invention, gigaHertz (GHz) frequencies can be administered to the patient (these signals have wavelengths on the order of millimeters, near the boarder in the electromagnetic spectrum where "light" waves meet "radio" waves). In particular, the GHz signal is preferably provided as a bipolar signal. It is also preferred that the GHz signal be provided in the gap (silence) in the combined waveform when the first modulation is off the duty cycle, as shown in FIG. 1G; it can also be seen that the GHz signal likewise occurs when the duty cycle of the combined waveform-modulated TENS signal is off. For the UHF signal (ultrahigh frequency, i.e., the GHz signal), frequencies of 1 KHz to 300 GHz, preferably 100 MHz to 200 GHz, more preferably 20–100 GHz, and most preferably 50–75 GHz are used.

As just described, and as shown in the Figures, the combined waveform, the TENS signal, and the GHz signal can be considered to be synchronized, the TENS signal being modulated by the combined waveform and the GHz signal occurring opposite thereto. In other embodiments, the TENS signal and/or the GHz signal can be administered asynchronously to the combined waveform and/or to each other; that is, the combined, TENS, and GHz signal can be in any combination of synchronicity or asynchronicity with each other.

Although the square waveforms in FIGS. 1A–1F may not be of uniform height, it is preferred that the total current delivered in any combination of signals administered to the patient be in the range of about one to about 50 ma.

The modulated waveform, with the optional bipolar spike waveform synchronous or asychronous therewith, can be administered to the patient using any of a number of the modulated subcombinations of signals as described herein. For example, using the waveforms depicted in FIG. 1, the patient can receive simultaneously the typical combined waveform of FIG. 1D and the TENS and/or bipolar stimulation signal (FIGS. 1E and 1F), and during the "off" portion of the duty cycle of these 'combined' waveforms there is adminstered the millimeter wave GHz frequency signal (FIG. 1G). On the other hand, all of the signals can be modulated together, or any combination can be used. In fact, based on the empirical nature of medical treatment, whether in Eastern or Western medicine, it would likely be beneficial to the care provider to try different combinations (i.e., mutual modulations) of these signals to determine with which particular combination the patient finds the most relief.

Figure 3:
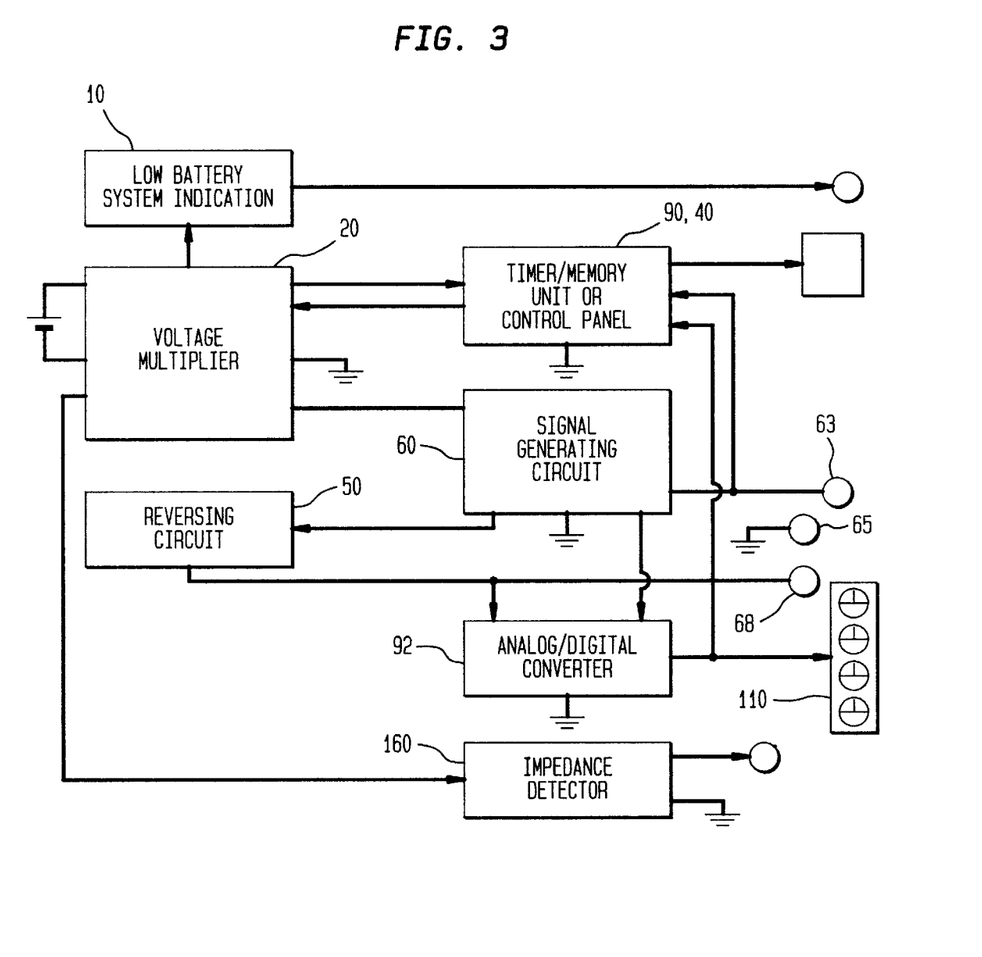
FIG. 3 is a block diagram of the inventive apparatus for generating the waveform depicted in FIG. 1.

Turning now to FIG. 3, the functional elements of the inventive device are presented. The power source to the present system will either be a battery having nominal 9 volt terminal voltage or some rectified and properly transformed line (AC) power source. The battery provides the basic DC power source for generating the complex waveform. This is channeled and controlled by the voltage multiplier, 20. The output of the voltage multiplier 20 which is between 27 v to 40 v, is fed to signal generating circuit 60 which is the oscillating circuit that converts the constant DC output into the complex waveform having the desired characteristics.

The specific constant current and current limited waveform generated by signal generating circuit 60 is pre-set by entering the various frequency settings for the two modulations, and the carrier. This may be entered manually through adjusting the settings on control panel 90. Alternatively, these settings may be stored in digital memory 40 as previously set values. The actual output of this system is regulated by monitor 70 which then provides the system output on a display, via control panel 90, or a memory value for subsequent retrieval from memory 40.

The signal generating circuit 60 receives the voltage of 27 v to 40 v from the voltage multiplier. Within the signal generating circuit 60, the voltage branches off into a carrier frequency and two modulation frequencies. An example of the branching of the waveform is depicted in FIGS. 1A–1C.

In FIG. 3, the system supports two separate probes for placement on the patient. Probe 63 represents the positive terminal as generated by signal generating 60. The second probe 65, is grounded within the circuit. For operation applying a bipolar waveform, the probes are connected to terminals 65 and 68, respectively. Terminal 68 is the output from reversing circuit 50, which may be present and which acts to flip the signal generating circuit pursuant to pre-set timing constraints.

The following ancillary systems are also present in this circuit. The low battery and system on indicator 10 which monitors the battery output via voltage multiplier 20 generates an alarm signal when battery output voltage drops below the pre-set limit, say 7.0 volts. It also shuts the system down if the battery voltage falls below the preset limit of approximately 6.0 volts.

The analog/digital converter 92 converts the signal from the signal generating circuit 60 so that the patient can read it. The analog/digital converter 92 reads the level of output and converts it to the appropriate signal for the four gate integrated circuit which uses that signal to turn on the appropriate sequence of four LEDs 110.

Finally the impedance detector 160 is used to determine if the system is being used on a person (as opposed to someone just running the system without attaching it to a person). While conventional impedence detection/determining apparatus uses an alternating 1000 cycle signal, it is preferred in the present invention to use the preferred 15 KHz cycle as a reference for matching impedance. Impedence is then measured by determining the voltage across the 15 KHz leads on the patient's body.

In other preferred embodiments, it is desirable for any device incorporating the present invention to have an indication verifying, if not also displaying, the impedance of the subject. In yet another preferred embodiment, it is desirable for such a device to have a detector to confirm the presence of millimeter wave energy; such a detector is constructed using a field detecting diode like analogous devices used for detecting laser energy (e.g., as in hand-held scanners).

Figure 4:
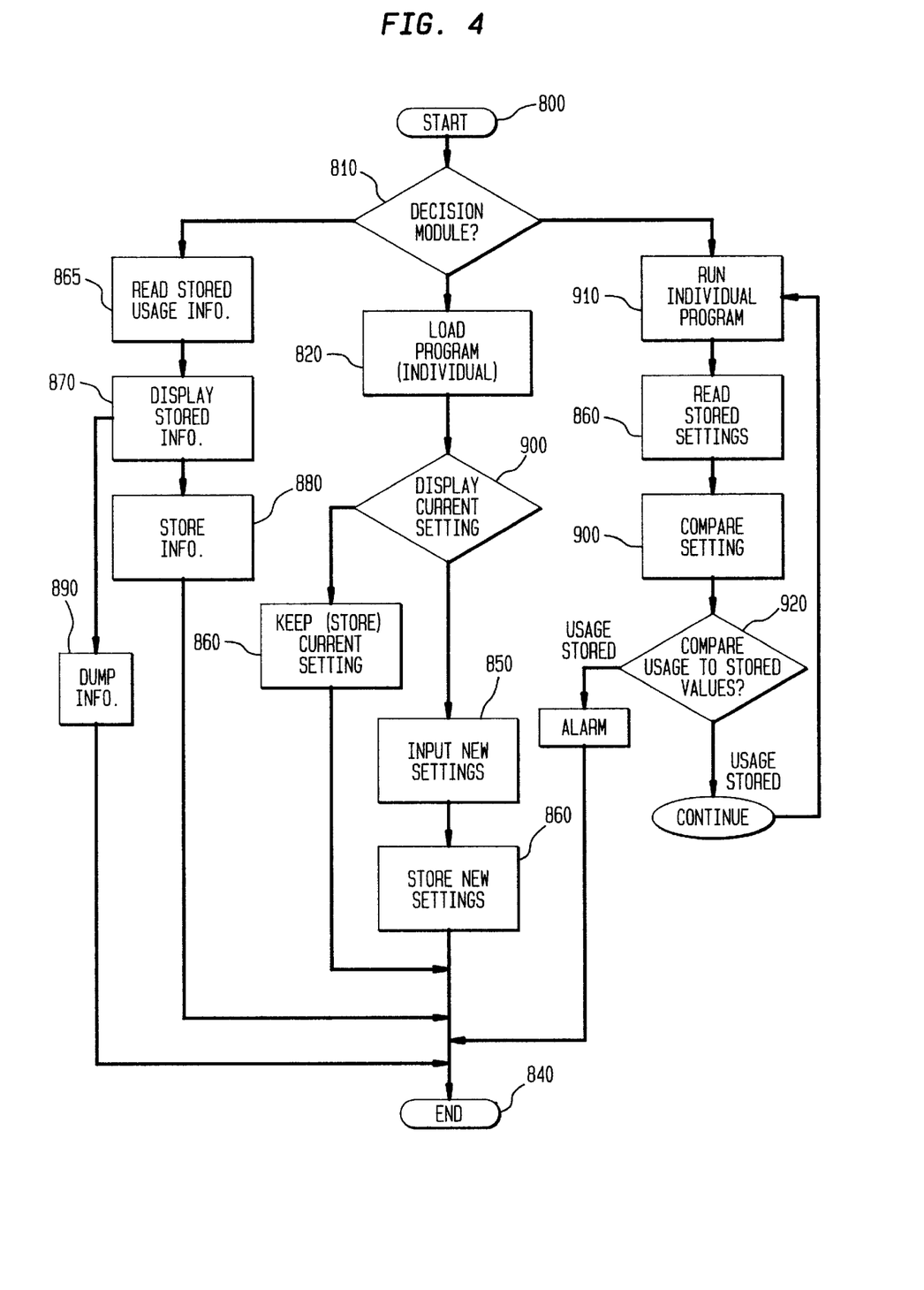
FIG. 4 is a logic flow chart of the data processing program controlling the operation of the apparatus of FIG. 2.

FIG. 4 depicts an exemplary flow chart of the timer unit 90 which the apparatus will use to monitor usage by the patient. A computer program embodying the protocol shown in the flow chart operating in combination with the present invention will prevent the patient from misusing the apparatus, and will allow the physician to set an individual treatment program and to monitor the patient's compliance to the set program.

The timer unit 90 will allow the therapist to set the number of days the system is to be used, the number of times per day the system will be used, and the time duration for each use. In various embodiments, conventional timing circuits, preferably with associated audible alarms, can be set to provide 1, 2, 3, 10, 20, 30, 40, or 60 minutes of administration the waveform, or any particular duration as is desirable for affecting the patient.

The program will start 800 with an Origination Decision module 810. The Origination Decision Module 810 will give the therapist three choices for use. If the Individualized Program 820 pathway is chosen, the timer unit will load the Individualized Program 820. Then the Individualized Program will begin with a display showing the Current Setting 900, for each of the parameters (i.e. the number of days of use, the number of times per day of use and the length of time for each use). Next the program will ask the therapist whether he wants to Keep the Current Settings 900, or Input New Settings 830. If the therapist wishes to use the same settings as are already registered in the program, the Individualized Program 820, will Store 860 the values and will End 840. However, if the therapist wishes to change the settings, the program will proceed to the Change Input Values 850 module in which the computer will ask the therapist for the new values for the settings. Then the computer will Store 860 the new values and will End 840.

Another selection which a therapist may make at the Origination Decision Module 810 is to read the stored information from the patient's system. If the therapist decides to access the Read Stored Results 865 module, the Setting and Use information will be displayed 870, and the therapist will decide whether to store the patient information in the Patient Storage Module 880, or else it will Dump the information 890 and it will End 840.

A final selection which the therapist may access through the Origination Decision Module 910, is actually to use the system. If this choice is the inputted selection, the Run Timed Program 910 will be initialized. The Run Timed Program 890 will read the stored 860 values. Then the program will Check 920 the Stored 860 values against the Current Running Settings 900 which is the values of the Run Timed Program 890 for this usage of the system. If the Current Running Settings 900 for the number of days of use is greater than the Stored 860 values, the program will End 840 without the system being turned on. Next, the Run Timed Program 890 will check the value of the Stored 890 values for the number of uses for a given day and if the Current Running Settings 900 is greater than the Stored 890 values for number of uses for a day, the system will End 840 for that day and the system will not be able to be used until the next day. Finally, as the system is being used, a Running Time Clock will be compared to the Run Timed Program, 890, and when the Current Running Settings in 900 is greater than the Stored 890 values for the length of time for that session, the system will End 840 for that session and the system will not be able to be used until the next session period.

In operation, it is preferred to use a conventional monopolar or bipolar waveform; generally, the monopolar should be attempted first and, if the patient does not find relief, a bipolar waveform is then attempted.

Figures 5A, 5B:
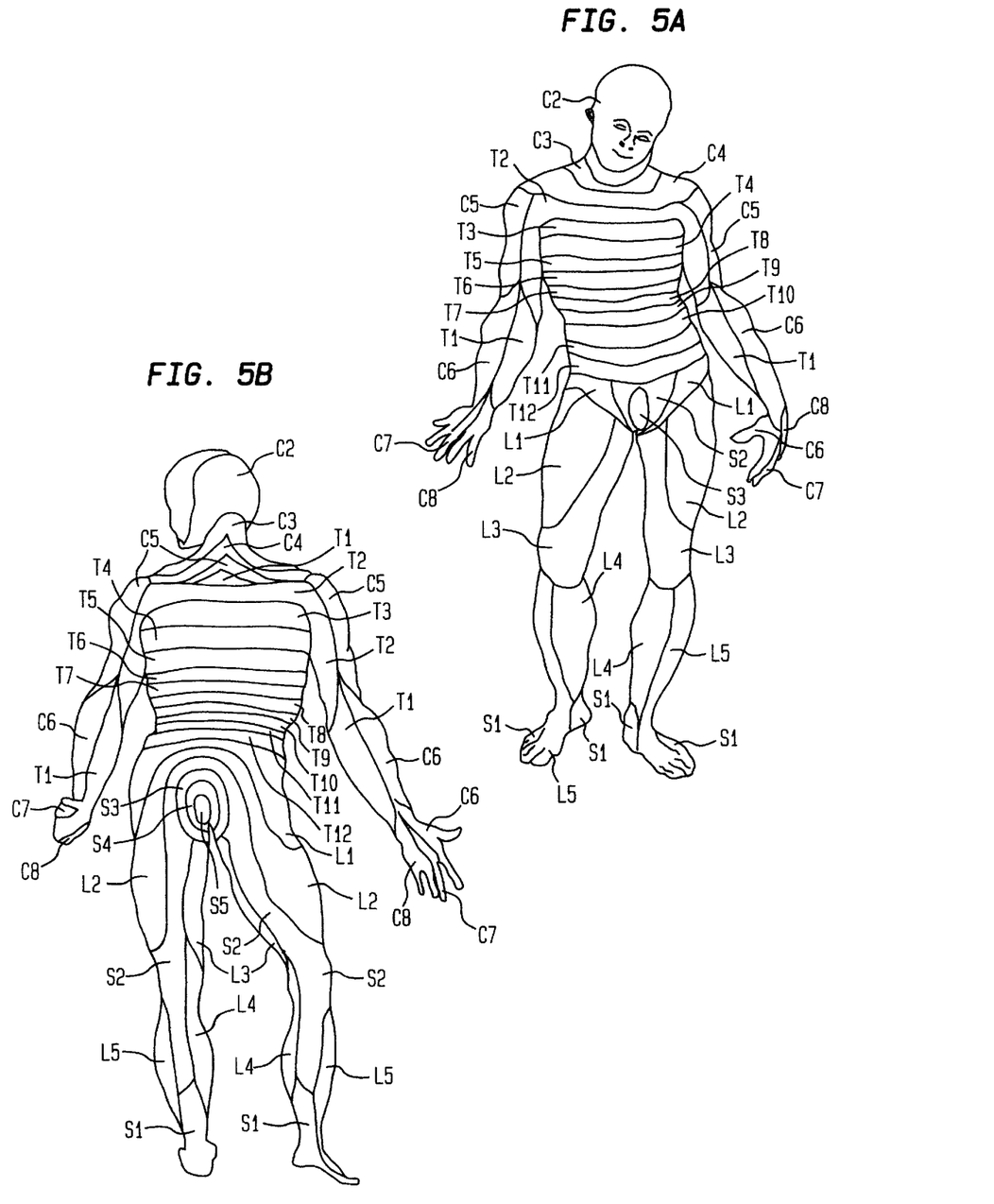
FIGS. 5A and 5B are, respectively, anterior and posterior views of human dermatomes overlaid on a figure from A. Versalius' *De Humani Corporis Fabrica* (1555).
Figure 6A:
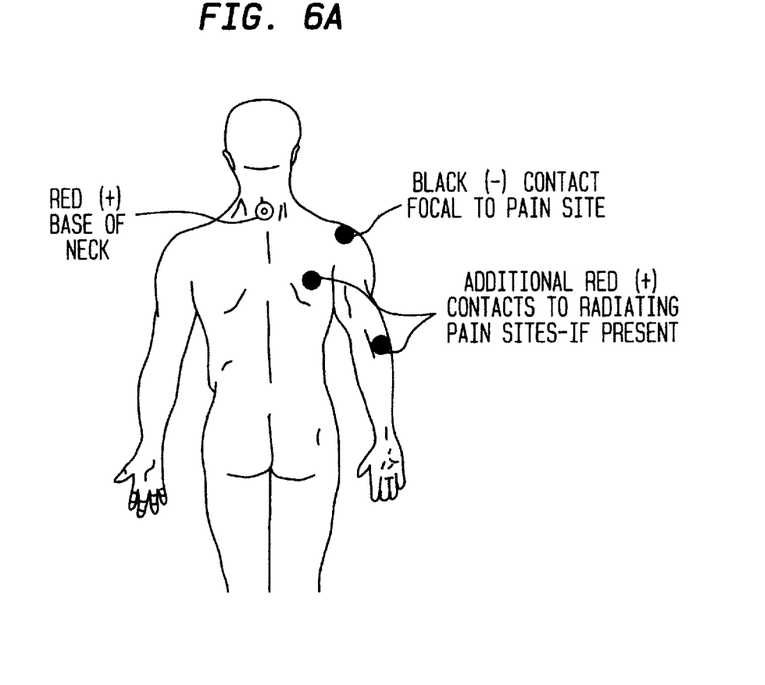
FIGS. 6A–6D show examples of the placement of electrodes on a patient for administering the therapeutic waveforms of the present invention to such patient.
Figure 6B:
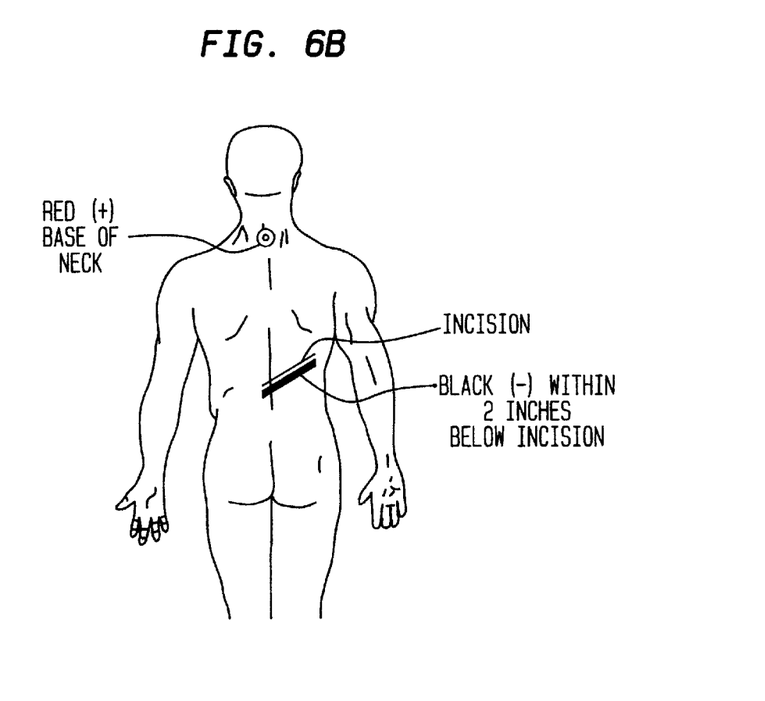
Figure 6C:
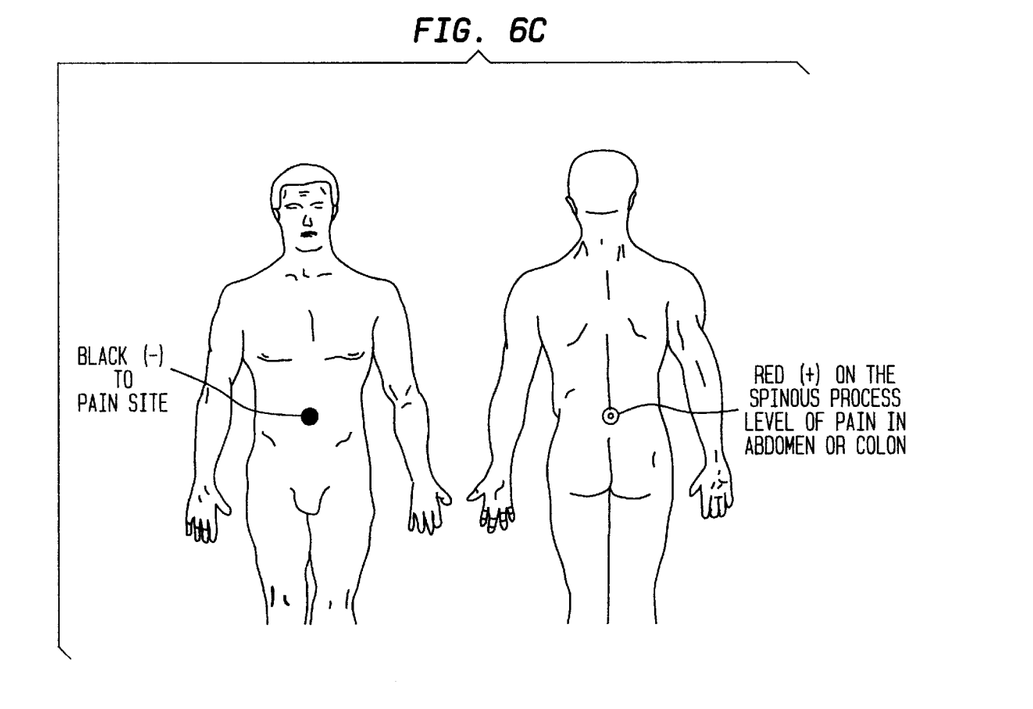
Figure 6D:
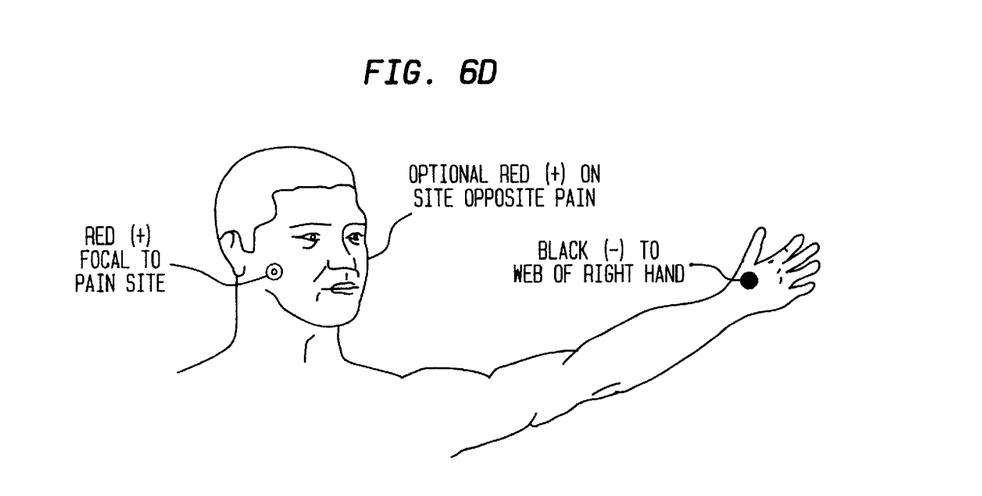
Figure 7A:
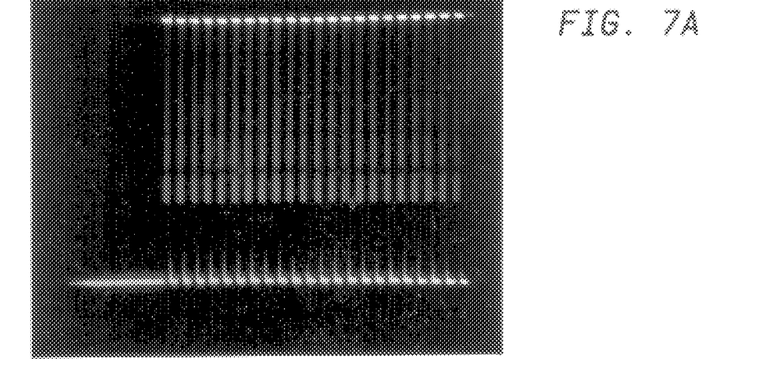
FIGS. 7A–7C depict oscilloscope tracings showing the resistive load (7A) of a human body subject to the present system as well as the capacitive load (7B–7C).
Figure 7B:
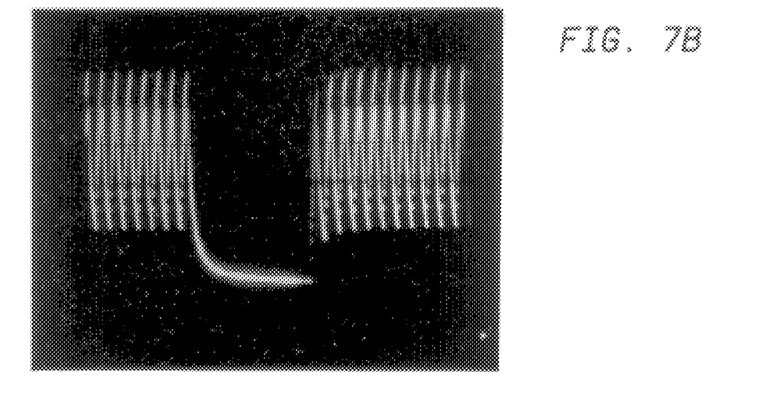
Figure 7C:
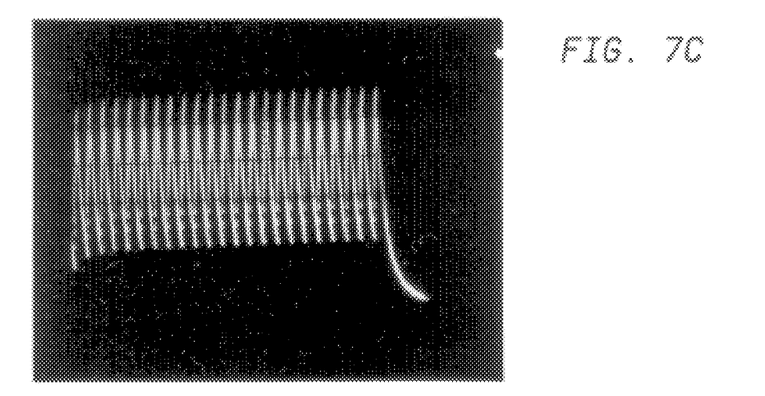

The modulated combined waveform (combined waveform modulation of a gigaTENS signal, optionally including a synchronous or asynchronous conventional spike waveform) is transmitted to the patient preferably using physiologically related reactive sites on the body. These sites can be derived from the meridians of acupuncture, from Chakra trigger points, from Shiatsu trigger points, or from dermatomes (neurogenic), myotomes (myogenic), or sclerotomes (osteogenic); examples of dermatomes on the male human body are shown in FIGS. 5A and 5B. In general, these "physiologically related reactive sites" effectively join what may appear as anatomically distant sites on the body but which, by Western, Eastern, or other acknowledged standards, are actually related to the same physiological condition. See. e.g., J. J. Keegan et al., "The Segmental Distribution of the Cutaneous Nerves in the Limbs of Man," Anat. Rec., 102:409 (1948); J. H. Martin, "Somatic Sensory System II: Anatomical Substrates for Somatic Sensation," in Principles of Neural Science, Ed. by E. R. Kandel et al. (North Holland, N.Y.: Elsevier, 1981); and Janet G. Travel et al., Myofascial Pain and Dysfunction: The Trigger Point Manual (Baltimore, Md.: Williams & Wilkins) (defining a "trigger point" as a focus of hyperirritability in a tissue that, when compressed, is locally tender and, if sufficiently hypersensitive, give rise to referred pain and tenderness, and sometimes to referred autonomic phenomena and distortion of proprioception).

In general, the combined modulated waveform is preferably administered to the patient using electrodes. The positive electrode is typically placed on the spinous process and the negative electrode is placed distally of the positive electrode with respect to the location of the discomfort perceived by the patient. (It is not uncommon that alleviating one symptom will expose a prior existing condition which may, in fact, have been the cause of the perceived pain or other problem.) More particularly, the negative electrode(s) are preferably placed in the dermatome (or myotome or sclerotome, or along the acupuncture meridian, etc.) corresponding to the location of discomfort as well as distally from such location. Alternatively, for example, it may be desirable to place the negative electrode (or another negative electrode) at the point of insertion of the muscle apparently associated with the myotome of the location of the discomfort. (As is typical in the medical arts, treatment is performed on a empirical basis due to the unpredictability of many treatments.)

As an example, if treatment of a patient using conventional TENS therapy is ineffective, the present invention can be used, with the electrodes placed as describe, and the intensity is increased until the patient feels any of the typical stimulation sensations (itching, pins and needles, warmth, or an insect-biting sensation). The intensity is then decreased and maintained just at subthreshold of this sensation (with further adjustments in intensity depending upon the patient's sensations). The treatment time is preferably for about 10 to about 60 minutes, and the skin condition is typically observed every 10 to 20 minutes to check for irritation. In another mode, where the equipment is so designed, the patient is immersed in a bath (preferably at least warm), the positive electrode is placed on the spinous process at the back of the neck above the water line, and the negative electrode is placed in the water for whole body stimulation (only low, microcurrents should be used).

This invention can be used in the treatment and/or prophylaxis of such conditions as migraine headaches, tension headaches, sinus headaches, tic doloreux, TMJ (tribomandibular joint) syndrome, post-herpetic facial neuralgia, stress, spasticity, depression, drug dependence or withdrawal, anxiety, insomnia, general or localized muscle pain (e.g., neck, shoulder (e.g., bursitis), elbow (e.g., tennis elbow), back (e.g., sciatica), wrist (e.g., carpal tunnel syndrome and other repetitive motion disorders)), post-operative pain, arthritis, phantom limb pain, finger pain, shingles, decubitus ulcers, gastroenterological pain, and other maladies. FIGS. 6A–6D depict schematic representations of electrode placements for treating various maladies, specifically (in respect of the figures) bursitis, postoperative pain, GI pain, and TMJ pain. In general, blood flow is increased towards the negative electrode.

The embodiment of the above description has been based on discrete components to enhance the understanding of the functional characteristics of the system. Numerous modifications and adaptations thereof will be readily apparent to those skilled in the art without departing from the spirit and scope of the present invention.

What is claimed is:

1. In combination, in a system for the treatment of certain neural responsive conditions, said system comprising:
    A. means for generating a carrier frequency in the range of between 1 KHz and 300 GHz;
    B. means for modulating said carrier at a frequency between 0.01 and 199 KHz; and
    C. means for further modulating the carrier at a frequency in the range between 0.1 and 300 KHz; to produce a combined waveform;
    D. means for further modulating the carrier frequency by generating a millimeter waveform in the GHz frequency range and modulating said carrier therewith to provide a gigahertz-modulated combined waveform; and
    E. electrodes for applying said gigahertz-modulated combined waveform to a patient in need thereof.

2. The system of claim 1, further comprising means for generating a monopolar or bipolar spike waveform.

3. The system of claim 2, wherein the spike waveform has a frequency in the range of 1 to 256 Hz.

4. The system of claim 3, wherein the spike waveform has at least one discrete frequency of $2^n$ where 0<n<8.

5. The system of claim 2, wherein said spike waveform is modulated by said carrier (A), said modulation (B), said further modulation (C), or a combination thereof.

6. The system of claim 2, wherein said spike waveform is asynchronous with said other waveforms and modulations.

7. The system of claim 5, wherein said millimeter waveform is modulated by said carrier (A), said modulation (B), said further modulation (C), said spike waveform, or a combination thereof.

8. In combination, in a method for the treatment of certain neural responsive conditions, said method comprising
    (i) providing a stimulating signal comprising:
        A. a carrier frequency in the range of between 1 KHz and 300 GHz;
        B. a modulation of said carrier at a frequency between 0.01 and 199 KHz; and
        C. a further modulation of said carrier at a frequency in the range between 0.1 and 300 KHz; to produce a combined waveform; and
        D. a further modulation of said carrier using a millimeter waveform in the GHz frequency range to produce a gigahertz-modulated combined waveform; and
    (ii) administering said pigahertz-modulated combined waveform to a patient in need thereof.

9. The system of claim 8, wherein said waveform (D) is modulated by said combined waveform.

10. The method of claim 9, wherein said modulated combined waveform is administered to the patient through electrodes.

11. The method of claim 10, wherein said electrodes are placed on said patient such that during said administration one electrode is on the patient's spinous process and the other electrode is positioned on the patient distally from the location of the condition.

12. The method of claim 11, wherein the electrodes comprise positive and negative electrodes, and the positive electrode is position on the patient's spinous process.

13. The system of claim 8, further comprising means for generating a monopolar or bipolar spike waveform.

14. The system of claim 13, wherein the spike waveform has a frequency in the range of 1 to 256 Hz.

15. The system of claim 14, wherein the spike waveform has at least one discrete frequency of $2^n$ where 0<n<8.

16. The system of claim 13, wherein said spike waveform is modulated by said carrier (A), said modulation (B), said further modulation (C), or a combination thereof.

17. The system of claim 13, wherein said spike waveform is asynchronous with said other waveforms and modulations.

* * * * *